US007938339B2

(12) United States Patent
Robert et al.

(10) Patent No.: US 7,938,339 B2
(45) Date of Patent: May 10, 2011

(54) NOZZLE ASSEMBLY FOR A WASHER

(75) Inventors: Maxime Robert, L'Ancienne-Lorette (CA); Élie Couture, Quebec (CA); Ghislain Parent, Saint-Isidore (CA)

(73) Assignee: Steris Inc., Temecula, CA (US)

( * ) Notice: Subject to any disclaimer, the term of this patent is extended or adjusted under 35 U.S.C. 154(b) by 509 days.

(21) Appl. No.: 11/934,306

(22) Filed: Nov. 2, 2007

(65) Prior Publication Data
US 2009/0114741 A1    May 7, 2009

(51) Int. Cl.
*B05B 3/02* (2006.01)
(52) U.S. Cl. ............... 239/214.15; 239/73; 239/222; 239/225.1; 134/176
(58) Field of Classification Search ............ 239/71, 239/73, 159–170, 206, 214.15, 222, 222.13, 239/225.1, 231, 237, 243, 247, 251, 264; 134/176, 179
See application file for complete search history.

(56) References Cited

U.S. PATENT DOCUMENTS

| 169,355 | A |  | 11/1875 | Grinnell | 408/44 |
| 528,144 | A |  | 10/1894 | Cadwell | 54/21 |
| 1,922,259 | A |  | 8/1933 | Paradise | 299/106 |
| 2,557,206 | A |  | 6/1951 | Spender | 299/69 |
| 2,574,874 | A | * | 11/1951 | Koeppel | 239/247 |
| 2,665,946 | A |  | 1/1954 | Broughton | 299/104 |
| 2,714,244 | A |  | 8/1955 | Shepard | 29/157 |
| 2,714,530 | A |  | 8/1955 | Shepard | 299/104 |
| 2,834,635 | A |  | 5/1958 | Miller | 299/104 |
| 2,905,393 | A |  | 9/1959 | Federighi et al. | 239/110 |
| 3,209,575 | A |  | 10/1965 | Woodward, Jr. et al. | 72/327 |
| 3,323,529 | A |  | 6/1967 | Geiger et al. | 134/104.1 |
| 3,357,644 | A | * | 12/1967 | Penfield et al. | 239/231 |
| 3,744,721 | A |  | 7/1973 | Baumstark, Jr. | 239/261 |
| 3,893,628 | A |  | 7/1975 | McCollum | 239/521 |
| 3,913,845 | A |  | 10/1975 | Tsuji | 239/556 |
| 3,943,951 | A |  | 3/1976 | Spotz | 134/100 |

(Continued)

FOREIGN PATENT DOCUMENTS
DE   10 2006 007 329   8/2007

(Continued)

OTHER PUBLICATIONS

Extended European Search Report for EP 08845156.2, dated Dec. 10, 2010.

*Primary Examiner* — Jason J Boeckmann
(74) *Attorney, Agent, or Firm* — Kusner & Jaffe; Michael A. Centanni

(57) ABSTRACT

The present invention provides a spray arm assembly comprised of a tubular member rotatable about a fixed axis. The tubular member has an internal passage and a central axis extending a length of the tubular member. A nozzle assembly is attachable to an end of the tubular member and fluidly communicates with the internal passage of the tubular member. The nozzle assembly is comprised of an insert attachable to the tubular member in a predetermined position. A nozzle body has an aperture therein defining a spray orifice. The nozzle body is mountable to the insert in one of a plurality of positions wherein the spray orifice has an orientation based upon a position of the nozzle body relative to the insert. A fastening means is provided for fastening the insert and the nozzle body together in one of the plurality of positions.

7 Claims, 5 Drawing Sheets

U.S. PATENT DOCUMENTS

| | | | |
|---|---|---|---|
| 3,958,255 A | 5/1976 | Chiou et al. | 346/140 |
| 3,980,104 A | 9/1976 | Kabai | 23/288 |
| 4,078,727 A | 3/1978 | Lingnau | 239/247 |
| 4,278,101 A | 7/1981 | Tanaka et al. | 134/167 |
| 4,435,891 A | 3/1984 | Nicholson | 29/157 |
| 4,579,284 A | 4/1986 | Arnold | 239/381 |
| 4,582,259 A | 4/1986 | Hoover et al. | 239/559 |
| 4,733,823 A | 3/1988 | Waggener et al. | 239/601 |
| 5,065,944 A | 11/1991 | D'Amato | 239/550 |
| 5,095,925 A | 3/1992 | Elledge et al. | 134/61 |
| 5,096,746 A | 3/1992 | Strizki | 427/236 |
| 5,220,933 A | 6/1993 | Albers | 134/58 |
| 5,225,160 A | 7/1993 | Sanford et al. | 422/28 |
| 5,307,993 A * | 5/1994 | Simonetti et al. | 239/247 |
| 5,472,143 A | 12/1995 | Bartels et al. | 239/462 |
| 5,666,050 A | 9/1997 | Bouldin et al. | 324/207.26 |
| 5,673,714 A * | 10/1997 | Campagnolo et al. | 134/57 D |
| 5,749,385 A | 5/1998 | Rochette et al. | 134/199 |
| 6,161,780 A | 12/2000 | Sugimoto et al. | 239/533.12 |
| 6,336,764 B1 * | 1/2002 | Liu | 401/289 |
| 6,394,369 B2 | 5/2002 | Goenka et al. | 239/601 |
| 6,398,136 B1 | 6/2002 | Smith | 239/600 |
| 6,533,991 B1 | 3/2003 | Moller | 266/250 |
| 6,578,369 B2 | 6/2003 | Kunkel et al. | 62/64 |
| 6,582,654 B1 | 6/2003 | Kral et al. | 422/28 |
| 6,585,943 B1 | 7/2003 | Sanford et al. | 422/307 |
| 6,884,392 B2 | 4/2005 | Malkin et al. | 422/26 |
| 7,207,198 B2 | 4/2007 | Benda | 70/19 |
| 2001/0017323 A1 * | 8/2001 | Feller et al. | 239/252 |
| 2002/0185165 A1 | 12/2002 | Lee et al. | 134/199 |
| 2004/0094190 A1 | 5/2004 | Robert | 134/108 |
| 2006/0208111 A1 | 9/2006 | Tracy et al. | 239/587.2 |
| 2007/0011805 A1 | 1/2007 | Shien | 4/615 |
| 2007/0235568 A1 | 10/2007 | Wang et al. | 239/562 |

FOREIGN PATENT DOCUMENTS

| | | |
|---|---|---|
| EP | 53231 A1 * | 6/1982 |
| FR | 545951 | 1/1922 |
| WO | WO 2007/021190 | 2/2007 |

* cited by examiner

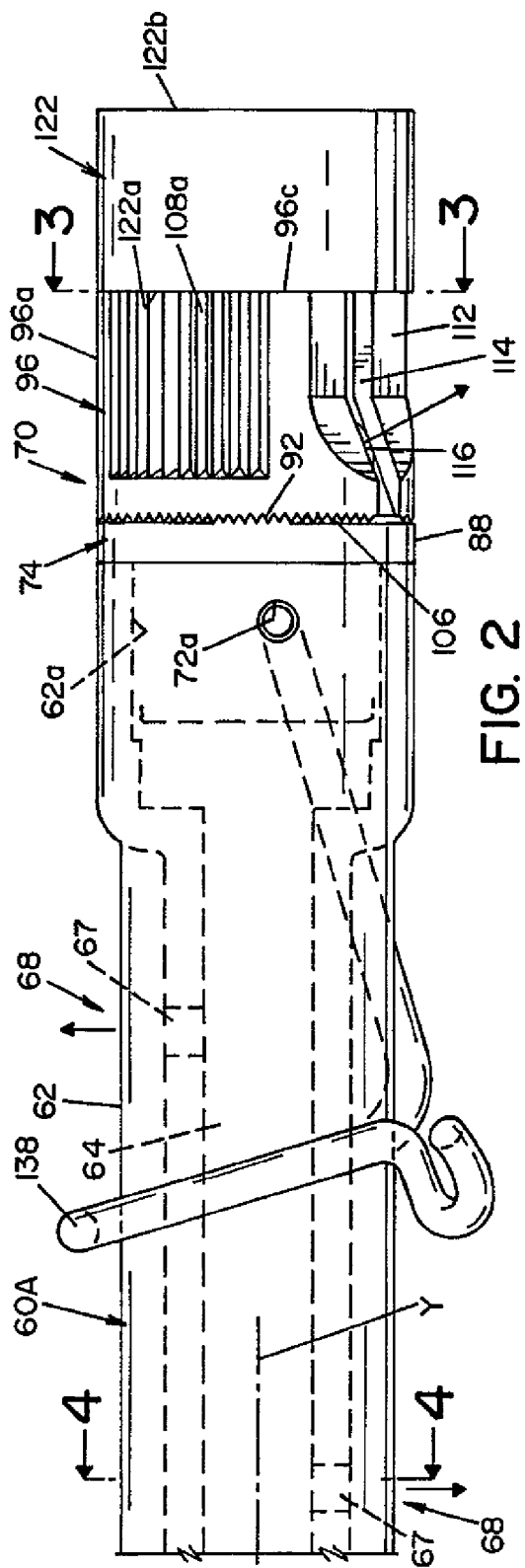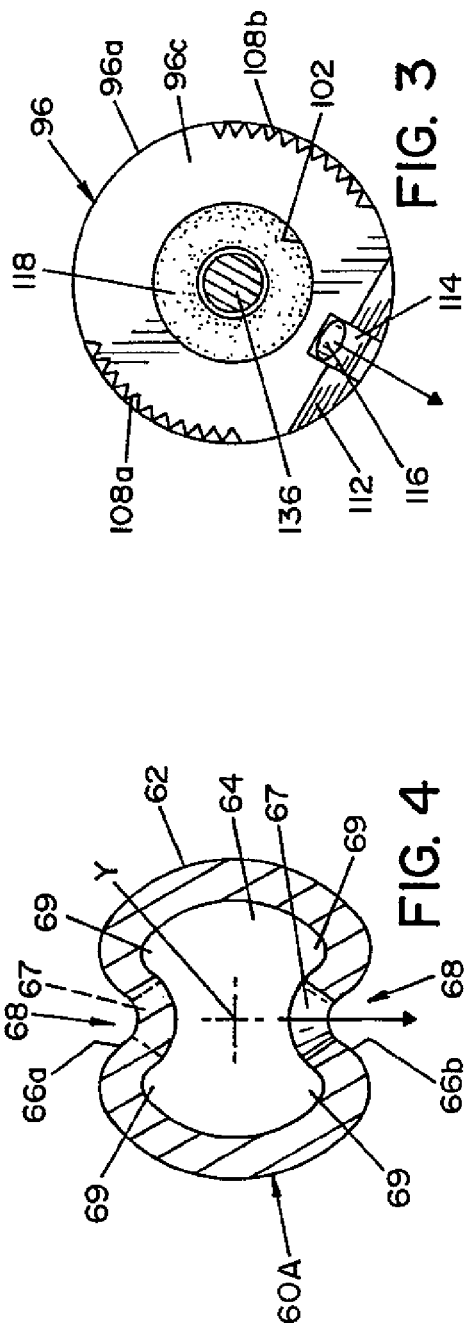

NOZZLE ASSEMBLY FOR A WASHER

FIELD OF THE INVENTION

The present invention relates to microbial deactivation of medical, dental, pharmaceutical, veterinary or mortuary instruments and devices, and more particularly to a spray arm for use in a washer decontamination system.

BACKGROUND OF THE INVENTION

Medical, dental, pharmaceutical, veterinary or mortuary instruments and devices that are exposed to blood or other body fluids require thorough cleaning and microbial deactivation between each use. Washer decontamination systems are now widely used to clean and deactivate instruments and devices that cannot withstand the high temperatures of a steam sterilization system. Washer decontamination systems typically operate by exposing the medical devices and/or instruments to a washing solution and/or heated water for thermal disinfection.

In such systems, the instruments or devices to be cleaned are typically placed within a rack that is dimensioned to be received into a chamber within the washer decontamination system. During a deactivation cycle, a circulation system circulates a liquid disinfectant to nozzles located in the chamber. The nozzles spray the liquid disinfectant onto the items disposed in the chamber thereby microbially deactivating them. Following the deactivation cycle, a rinse solution, typically water, is circulated to the nozzles. The nozzles spray the rinse solution on the items in the chamber to remove traces of the liquid disinfectant and any particulate that may have accumulated on the instruments or devices during the deactivation cycle.

In some systems, rotatable spray arms having nozzles formed therein, are disposed in the chamber to provide better coverage. In some applications, it is desirable to be able to adjust the direction of a spray nozzle or to be able to vary the speed of rotation of a rotatable spray arm.

The present invention provides an improved nozzle assembly wherein the direction of coverage of a nozzle can be adjusted and the speed of a rotational spray arm can be varied.

SUMMARY OF THE INVENTION

In accordance with one embodiment of the present invention, there is provided a spray arm assembly comprised of a tubular member rotatable about a fixed axis. The tubular member has an internal passage and a central axis extending a length of the tubular member. A nozzle assembly is attachable to an end of the tubular member and fluidly communicates with the internal passage of the tubular member. The nozzle assembly is comprised of an insert attachable to the tubular member in a predetermined position. A nozzle body has an aperture therein defining a spray orifice. The nozzle body is mountable to the insert in one of a plurality of positions wherein the spray orifice has an orientation based upon a position of the nozzle body relative to the insert. A fastening means is provided for fastening the insert and the nozzle member together in one of the plurality of positions.

In accordance with another embodiment of the present invention, there is provided a nozzle assembly comprised of an insert attachable to a tubular member. A nozzle body has an aperture therein. The aperture directs a spray of fluid in a predetermined direction relative to the nozzle body. The nozzle body is mountable to the insert in one of a plurality of positions wherein a direction of fluid exiting from the nozzle body through the aperture is adjustable relative to the tubular member. A fastening means is provided for fastening the insert and the nozzle member together in one of the plurality of mounting positions.

One advantage of the present invention is a nozzle assembly for use in a washer.

Another advantage of the present invention is a nozzle assembly for use on a spray arm.

Another advantage of the present invention is a nozzle assembly for use on a rotatable spray arm.

Yet another advantage of the present invention is nozzle assembly as described above, that can be repositioned relative to a spray arm.

Another advantage of the present invention is a spray arm assembly as described above, wherein the rotational speed of the spray arm can be modified based on the position of a nozzle relative to the spray arm.

Yet another advantage of the present invention is a spray arm assembly as described above, including a sensor element that allows for monitoring of the position of the spray arm.

Another advantage of the present invention is a spray arm assembly, as described above, wherein the nozzle assembly is removable from the spray arm assembly to facilitate the cleaning of an interior of the spray arm assembly.

Yet another advantage of the present invention is a spray arm assembly, as described above, wherein the nozzle assembly is removable from the spray arm assembly without removing the spray arm assembly from the washer.

These and other advantages will become apparent from the following description of one embodiment taken together with the accompanying drawings and the appended claims.

BRIEF DESCRIPTION OF THE DRAWINGS

The invention may take physical form in certain parts and arrangement of parts, one embodiment of which will be described in detail in the specification and illustrated in the accompanying drawings which form a part hereof, and wherein:

FIG. 2 is an enlarged view of one end of a spray arm showing a preferred embodiment of the present invention;

FIG. 3 is a cross sectional view taken along lines 3-3 in FIG. 2;

FIG. 4 is a cross section view taken along lines 4-4 in FIG. 2;

DETAILED DESCRIPTION OF THE INVENTION

Figure 1:
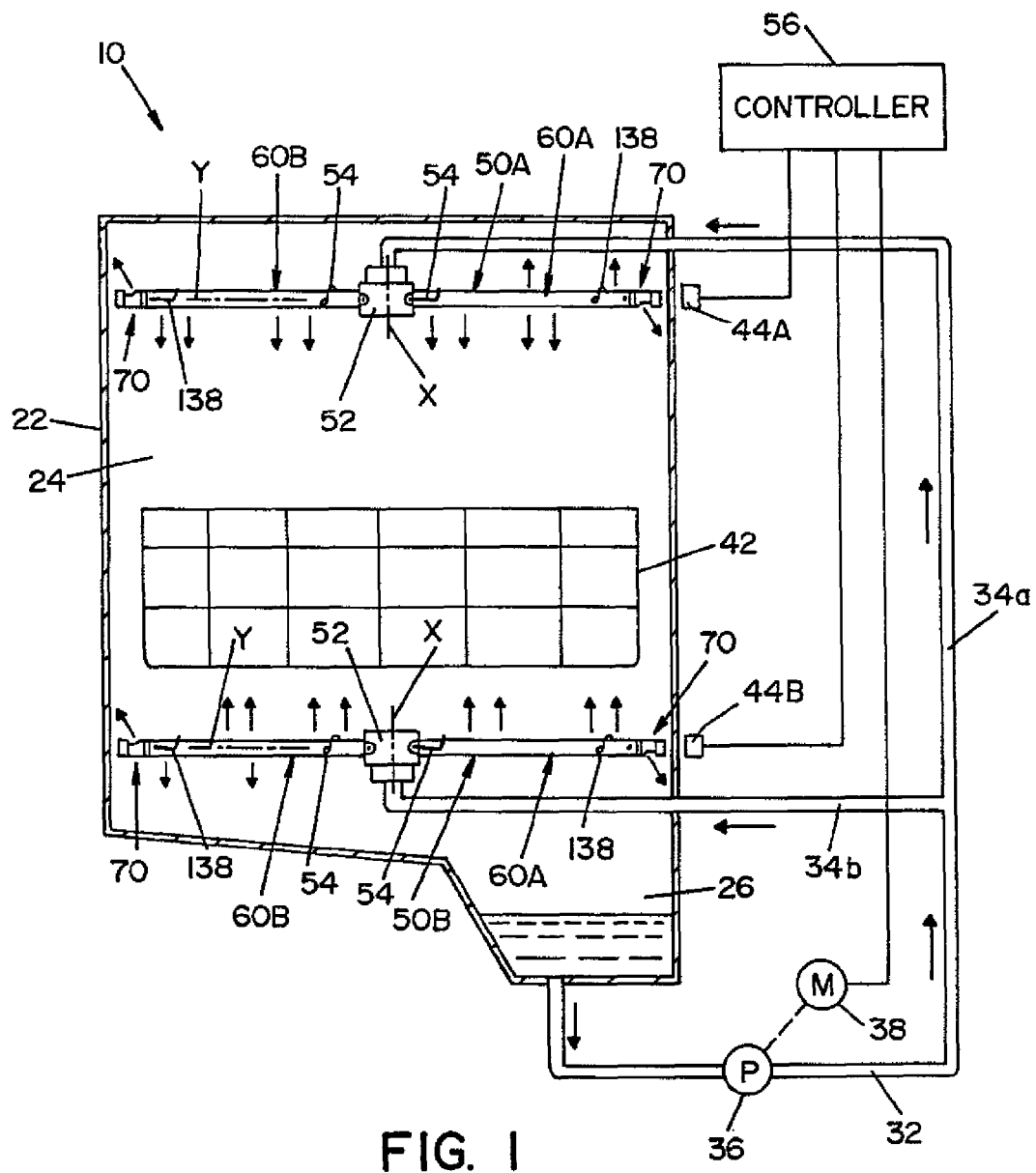
FIG. 1 is a schematic view of a washer decontamination system.

Referring now to the drawings wherein the showings are for the purpose of illustrating one embodiment of the invention only, and not for the purpose of limiting same. FIG. 1 shows a schematic view of a washer 10. In the embodiment shown, washer 10 is a washer decontamination system wherein medical instruments and/or devices may be deactivated. However, as will be appreciated from a reading of the specification, the present invention may find advantageous application in other types of washers and other apparatus wherein a fluid is sprayed.

Washer 10 is generally comprised of a housing 22 that defines a chamber 24. Housing 22 is formed to include a sloped sump 26 that is disposed at the bottom of chamber 24. Sump 26 is provided to receive washing or rinsing fluids, as will be described in greater detail below.

A circulation conduit 32 fluidly connects sump 26 to first and second branch conduits 34a, 34b having upper and lower spray arm assembly 50A, 50B attached thereto. First branch conduit 34a extends through a side wall of housing 22 and has an end disposed in an upper portion of chamber 24 with upper spray arm assembly 50A attached thereto. Second branch conduit 34b extends through the side wall of housing 22 and has an end disposed in a lower portion of chamber 24 with lower spray arm assembly 50B attached thereto. A pump 36 is provided within circulation conduit 32 for pumping fluids from sump 26 to spray arm assemblies 50A, 50B. A motor 38, schematically illustrated in the drawing, drives pump 36.

Washer 10 is dimensioned to contain one or more racks 42. Rack 42 is dimensioned to hold an instrument and/or device to be washed. Rack 42 is disposed between the upper and lower spray arms 50A, 50B, as shown in FIG. 1.

Upper and lower monitoring elements 44A, 44B are spaced away from the side walls of housing 22 at locations relative to spray arm assemblies 50A, 50B, respectively, as seen in FIG. 1. Upper and lower monitoring elements 44A, 44B are located outside of chamber 24 to isolate elements 44A, 44B from moisture in chamber 24. Upper and lower monitoring elements 44A, 44B are operable to sense spray arm assemblies 50A, 50B, respectively, during an operation of washer 10, as shall be described in greater detail below.

A controller 56 is operable to control motor 38 and receive signals from sensing elements 44A, 44B. In this respect, controller 56 controls the flow of fluid through circulation conduit 32 and monitors the position of spray arm assemblies 50A, 50B.

Spray arm assemblies 50A, 50B are essentially identical and as such only upper spray arm assembly 50A will be described in detail. Spray arm assembly 50A is comprised of a central hub 52 with arm assemblies 60A, 60B extending therefrom, as shown in FIG. 1. Central hub 52 defines an internal cavity (not shown) that is in fluid communication with first branch conduit 34a. Central hub 52 is mounted to an end of first branch conduit 34a to rotate about a fixed axis 'X.' In this respect, spray arm assembly 50A rotates about fixed axis 'X.' In the embodiment shown, spray arm assembly 50A includes two arm assemblies 60A, 60B extending from central hub 52. It is also contemplated that more than two, equally-spaced arm assemblies may extend from central hub 52. A retaining clip 54 attaches each arm assembly 60A, 60B to central hub 52, as shown in FIG. 1.

In the embodiment shown, arm assemblies 60A, 60B are essentially identical. Accordingly, only one arm assembly 60A will be described in detail. Arm assembly 60A, as best seen in FIG. 2, is generally comprised of an elongated tubular member 62 having a central axis 'Y.' Tubular member 62 defines an internal passage 64 that extends a length of tubular member 62. A series of spaced-apart spray nozzles 68 extend through a wall of tubular member 62 at discrete locations along tubular member 62. In the embodiment shown, tubular member 62 is a cylindrical tube and spray nozzles 68 are generally deformed openings. Spray nozzles 68 are formed by first drilling cylindrical holes 67 in the wall of tubular member 62. Opposing sides of tubular member 62 are then deformed to define axially-extending grooves 66a, 66b that extend a length of tubular member 62. Holes 67 become conical-shaped when grooves 66a, 66b are formed in tubular member 62, as seen in FIG. 4. The conical-shaped holes 67 define spray nozzles 68 that have a distinct spray pattern. Channels 69 are formed in the inner wall of tubular member 62 when grooves 66a, 66b are formed therein.

Figure 7:
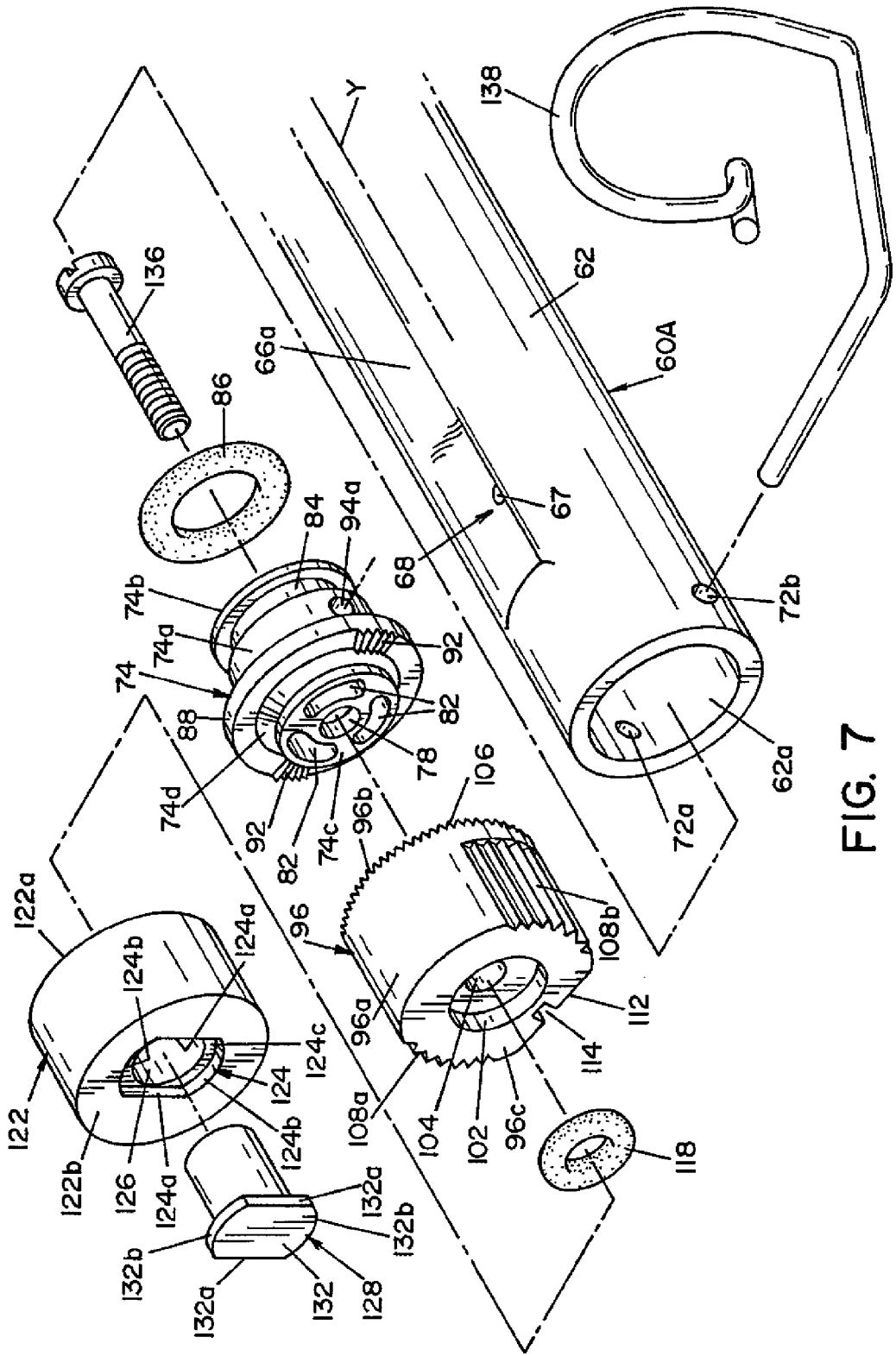
FIG. 7 is an exploded view of one end of the spray arm shown in FIG. 2.

A pair of holes 72a, 72b extend through the wall of tubular member 62 near the outward most end of tubular member 62. Holes 72a, 72b are aligned along a common axis, as best seen in FIG. 7. A counter bore 62a extends partially into the outward most end of tubular member 62. Counter bore 62a is dimensioned to receive a nozzle assembly 70.

Nozzle assembly 70 is attached to the distal end of each arm assembly 60A, 60B. Broadly stated, nozzle assembly 70 is comprised of an insert 74, a nozzle member 96 and a sensing element 122.

Figure 6:
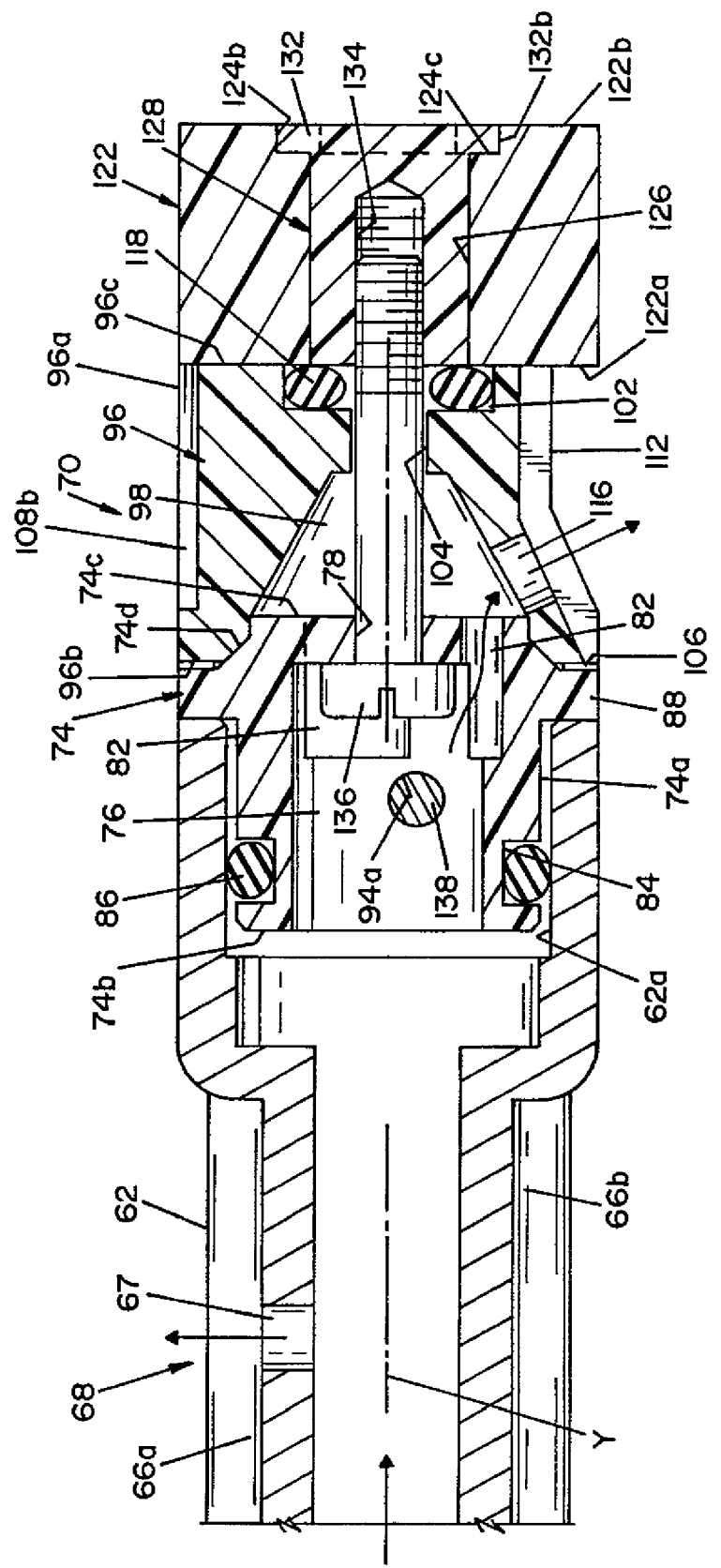
FIG. 6 is a cross sectional view of one end of the spray arm shown in FIG. 2.

Insert 74 is dimensioned to be disposed in the distal end of tubular member 62, as best seen in FIGS. 6 and 7. Insert 74 is generally cylindrical in shape with an outer surface 74a, a first end 74b and a second end 74c. An axially-aligned cylindrical recess 76 extends inwardly into first end 74b of insert 74. A hole 78 extends axially through second end 74c of insert 74 to communicate with recess 76. A series of arcuate slots 82 surround hole 78, as best seen in FIG. 7. Slots 82 communicate with recess 76, as best seen in FIG. 6. An annular groove 84 is formed in outer surface 74a of insert 74 near first end 74b. Groove 84 is dimensioned to accept a conventional o-ring 86 therein. A flange 88 extends outwardly from surface 74a of insert 74 near second end 74c. A conical surface 74d extends from flange 88 to surface 74a. A first series and a second series of surface projections 92 extend from the axially-facing surface of flange 88. Projections 92 are designed to matingly engage surface projections 106 of nozzle member 96, as shall be described in greater detail below. In the embodiment shown, surface projections 92 are triangular projections that extend radially outward from the axis of insert 74. Hole 94a, best seen in FIG. 7, and hole 94b (not shown) are formed in insert 74 and extend radially into recess 76. Holes 94a, 94b are aligned along a common axis.

Nozzle member 96 is designed to matingly engage insert 74. Nozzle member 96 is generally cylindrical in shape and has an outer surface 96a, a first end 96b and a second end 96c. A cavity 98 is formed in first end 96b of nozzle member 96. Cavity 98 is generally conical in shape. A cylindrical recess 102 is formed in second end 96c of nozzle member 96. A cylindrical and flat circular surface define recess 102. A conventional o-ring 118 is disposed in recess 102. A hole 104 extends axially through nozzle member 96 and communicates with cavity 98 and recess 102. Surface projections 106 are formed on an outward facing surface of nozzle member 96. Projections 106 are dimensioned to matingly engage projections 92 on insert 74, as shall be described in detail below. In the embodiment shown, projections 106 are triangular projections that extend radially inward from an edge of one end of nozzle member 96 to a chamfered surface of cavity 98.

Outer surface 96a of nozzle member 96 includes a first ribbed section 108a and a second ribbed section 108b. In the embodiment shown, first and second ribbed sections 108a, 108b are a series of triangular shaped projections that extend axially along surface 96a of nozzle member 96. First ribbed section 108a and second ribbed section 108b are disposed on opposite sides of nozzle member 96. A side of nozzle member 96 is cutaway to form a notch 112. In the embodiment shown, notch 112 is formed in surface 96a between first ribbed section 108a and second ribbed section 108b. Notch 112 defines two surfaces that are at angles relative to each other. A rectangular channel 114 is formed in the surfaces defined by notch 112 and extends from first end 96b to second end 96c.

An orifice 116 extends through a side wall of nozzle member 96 along an axis 'Z,' best seen in FIG. 6, to communicate with cavity 98.

A sensor element 122 is provided to mount to one end of nozzle member 96. Sensor element 122 is generally cylindrical in shape and has a first end 122a and second end 122b. A hole 126 extends axially through sensor element 122. A recess 124 is formed in an end surface of sensor element 122. Recess 124 defines two flat side surfaces 124a and two curved surfaces 124b disposed therebetween and a flat surface 124c. Sensor element 122 and upper and lower monitoring elements 44A, 44B are dimensioned relative to each other, as shall be described in greater detail below.

Opening 126 and recess 124 are dimensioned to receive a plug 128. Plug 128 is generally cylindrical in shape and includes a flange 132 extending outwardly from one end. An outer surface of flange 132 includes two flat outer surfaces 132a disposed between two curved outer surfaces 132b. A threaded bore 134 extends axially into plug 128 from another end of plug 128. Flat outer surfaces 132a and curved surfaces 132b are dimensioned to engage flat side surfaces 124a and curved surfaces 124b of sensor element 122, respectively. In one embodiment, plug 128 is made of a polymeric material.

Insert 74, nozzle member 96, and sensor element 122 are attached together by a conventionally known fastener 136. As shown in FIGS. 6 and 7, fastener 136 is dimensioned to have a length such that a head of fastener 136 is disposed in recess 76 of insert 74. A threaded end of fastener 136 extends through hole 78 of insert 74, through cavity 98 and hole 104 of nozzle member 96, and into threaded bore 134 of plug 128. In this respect, when fastener 136 is threaded into plug 128, a bottom surface of the slotted head of fastener 136 contacts a wall of recess 76 of insert 74. In a similar manner, an end surface of flange 132 of plug 128 contacts flat surface 124c of recess 124 in sensor element 122. As a result, fastener 136 and plug 128 apply an axial force to insert 74, nozzle member 96 and sensor element 122 to be secured together. O-ring 118 is disposed between sensor element 122 and nozzle member 96 and is dimensioned to create a fluid tight seal therebetween.

As stated above, projections 92 on insert 74 are dimensioned to engage projections 106 on nozzle member 96. In this respect, nozzle member 96 can be fixed in one of a plurality of positions relative to insert 74. Once nozzle member 96 is placed in the desired orientation, fastener 136 and plug 128 are tightened, as described above. Axis 'Z' of orifice 116 is fixed relative to nozzle member 96. In this respect, axis 'Z' of orifice 116 is also fixed in one of a plurality of positions relative to insert 74. A length of fastener 136 is dimensioned to allow plug 128 to be partially threaded off of fastener 136, i.e., loosened, such that nozzle member 96 can rotate with respect to insert 74, while still keeping nozzle member 96 restrained between insert 74 and sensor element 122. In this respect, an orientation of nozzle member 96 and orifice 116 can be varied without completely disassembling nozzle assembly 70.

As best seen in FIG. 6, nozzle assembly 70 is dimensioned to be received into counter-bore 62a of tubular member 62. Insert 74 of nozzle assembly 70 may be placed into tubular member 62 in one orientation. As stated above, nozzle member 96 and orifice 116 of nozzle assembly 70 may be placed in one of a plurality of positions relative to insert 74. In this respect, an orientation of nozzle member 96 and orifice 116 may be in one of a plurality of positions, relative to tubular member 62.

Figure 5:
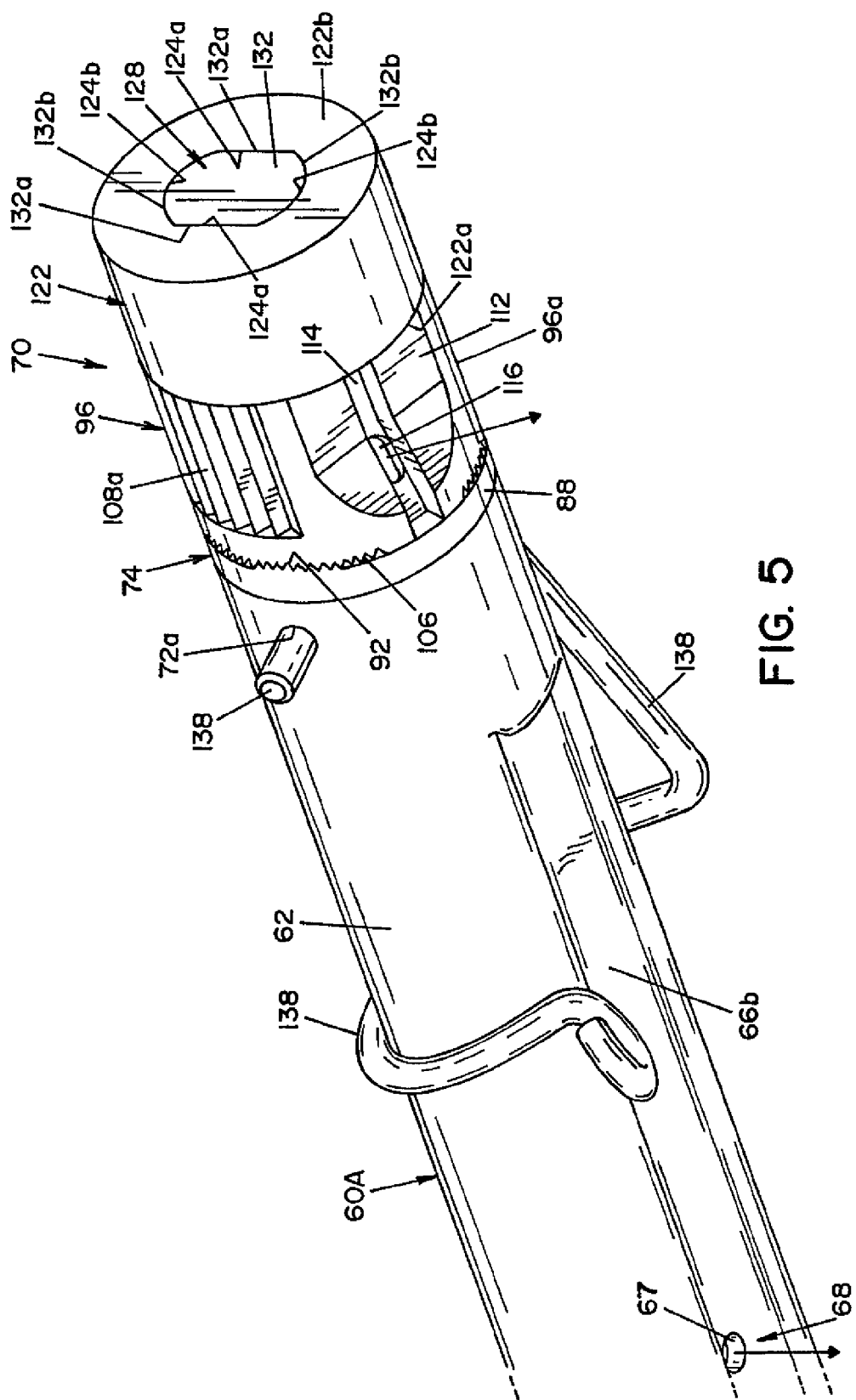
FIG. 5 is an isomeric view of one end of the spray arm shown in FIG. 2.

A retaining clip 138 is provided to attach nozzle assembly 70 to arm assembly 60A, 60B. Retaining clip 138 is generally a rod-shaped element with a straight end and a curved end. The straight end of retaining clip 138 has an outer diameter and the curved end is formed as shall be described in greater detail below. Retaining clip 138 is dimensioned to retain insert 74 within tubular member 62 by extending through holes 72a, 72b of tubular member 62 and through holes 94a, 94b of insert 74. Nozzle assembly 70 is placed into tubular member 62 such that holes 72a, 72b, 94a, 94b align. Holes 72a, 72b, 94a, 94b are all dimensioned to receive retaining clip 138 therein. The curve end of retaining clip 138 is dimensioned to rest on the outer surface of tubular member 62, as best shown in FIG. 5. Retaining clip 138 is therefore prevented from separating from tubular member 62. O-ring 86 is placed between an inner surface of tubular member 62 and insert 74. O-ring 86 is dimensioned to form a fluid tight seal between tubular member 62 and insert 74. In this respect, internal passage 64 is in fluid communication with cavity 76 in insert 74, oblong hole 82 in insert 74, first cavity 98 in nozzle member 96 and orifice 116 in nozzle member 96.

In the embodiment shown, nozzle member 96 is repositionable about axis 'Y' of tubular member 62 to position nozzle member 96 in one of a plurality of positions. As best seen in FIG. 6, axis 'Z' of orifice 116 is fixed relative to nozzle member 96 at a predetermined angle relative to axis 'Y' of tubular member 62. Therefore, axis 'Z' of orifice 116 is also repositionable about axis 'Y' of tubular member 62 to fix orifice 116 in one of a plurality of positions relative to axis 'Y' of tubular member 62.

The aforementioned embodiment of the invention shall now be further described with relation to the operation of washer 10. During a decontamination cycle in washer 10, water fills sump 26 from a source of water (not shown). Once filled to a desired level, controller 56 energizes pump 36 to cause fluid to circulate along circulation conduit 32, through first and second branch conduits 34a, 34b, through upper and lower spray arm assemblies 50A, 50B and back to chamber 24. In this respect, fluid flows through the cavity disposed in central hub 52, through internal passage 64 in tubular member 62, and exits through spray nozzle 68 in the wall of tubular member 62. Fluid exiting spray nozzles 68 creates sprays of water that impact the devices and/or instruments disposed in rack 42. Channels 69 in tubular member 62 define paths wherein fluid may flow toward the outward most end of tubular member 62.

A portion of the fluid that flows within internal passage 64 also passes through cavity 76 and holes 82 in insert 74, through cavity 98 and orifice 116 in nozzle member 96. Upon exiting orifice 116, the fluid creates a jet of high velocity water. The jet of water exiting orifice 116 creates a force that causes spray arm assemblies 50A, 50B to rotate about fixed axis 'X.' As stated above, nozzle member 96 is repositionable relative to insert 74 and tubular member 62 in one of a plurality of positions. In this respect, axis 'Z' of orifice 116 is repositionable to one of a plurality of positions relative to fixed axis 'X' about which spray arm assemblies 50A, 50B rotate. For each position of axis 'Z' of orifice 116, relative to fixed axis 'X,' there is a tangential component of force that causes upper and lower spray arm assemblies 50A, 50B to rotate. By varying the angle of axis 'Z' relative to axis 'X,' the speed of rotation of upper and lower spray arm assemblies 50A, 50B is also varied. In this respect, the present invention provides a structure wherein the orientation of an orifice 116 relative to an axis of rotation of a spray arm assembly 50A, 50B can be change to achieve a desired rate of rotation.

The rotation of spray arm assemblies 50A, 50B causes sensor element 122 to move along a predetermined path. Upper and lower monitoring elements 44A, 44B and sensor element 122 are dimensioned such that a portion of the predetermined path of sensor element 122 is within a predetermined distance from upper and lower monitoring elements 44A, 44B. In the embodiment shown, the path along which sensor element 122 moves is circular. In this embodiment, a portion of the circular path is within about 3 inches from upper and lower monitoring elements 44A, 44B. Upper and lower monitoring elements 44A, 44B are operable to sense when sensor element 122 passes within the predetermined distance from monitoring elements 44A, 44B. In this respect, upper and lower monitoring elements 44A, 44B are operable to provide a signal to the system controller 56 corresponding to the presence or absence of sensor element 122 next to upper and lower monitoring elements 44A, 44B. In one embodiment, the system controller 56 uses a signal from upper and lower monitoring elements 44A, 44B to determine a rate of rotation of upper and lower spray arm assemblies 50A, 50B, respectively.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is contemplated that racks 52 include one or more of the spray arm assemblies described above. The spray arm assemblies are connectable to a fluid inlet port (not shown) when racks 52 are disposed in chamber 24. The spray arm assemblies in racks 52 include the aforementioned nozzle assembly 70 that enable the spray arm assemblies to be detected by monitoring elements disposed outside of chamber 24, as described above. It is intended that all such modifications and alterations be included insofar as they come within the scope of the invention as claimed or the equivalents thereof.

Having described the invention, the following is claimed:

1. A spray arm assembly, comprised of:
   a tubular member rotatable about a fixed axis, said tubular member having an internal passage and a central axis extending a length of said tubular member; and
   a nozzle assembly attachable to an end of said tubular member and in fluid communication with said internal passage of said tubular member, said nozzle assembly comprised of:
      an insert attachable to said tubular member in a predetermined position;
      a nozzle body having an aperture therein defining a spray orifice, said nozzle body being attachable to said insert in one of a plurality of positions relative to said insert and wherein said spray orifice has an orientation based upon said position of said nozzle body relative to said insert wherein said nozzle body has a plurality of surface projections extending therefrom and said insert has a plurality of surface projections extending therefrom, said surface projections on said insert being dimensioned to matingly engage with said surface projections on said nozzle body, wherein said nozzle body is attachable to said insert in said one of said plurality of positions;
      a fastening means for securing said insert and said nozzle body together in said one of said plurality of positions; and
      a sensor element mounted to said nozzle body, wherein said fastening means extends through said insert and said nozzle body and threads into said sensor element such that said nozzle body is disposed between said insert and said sensor element.

2. A spray arm assembly as defined in claim 1, further comprised of:
   a monitoring element disposed along a path of said spray arm assembly relative to said sensor element, said monitoring element operable to provide a signal to a controller relative to a position of said sensor element.

3. A spray arm assembly as defined in claim 1, further comprising a retaining clip for attaching said insert to said tubular member in a fixed orientation relative to said tubular member.

4. A spray arm assembly as defined in claim 1, wherein said tubular member of said spray arm has a groove formed in an outer wall of said tubular member extending inwardly towards said internal passage, said groove extending parallel to said central axis of said tubular member.

5. A spray arm assembly as defined in claim 4, wherein spray holes extend through said outer wall of said tubular member at discrete locations along said groove, said spray holes fluidly communicating with said internal passage of said tubular member.

6. A spray arm assembly as defined in claim 5, wherein said spray holes spray downward and upward relative to said tubular member.

7. A spray arm assembly as defined in claim 1, wherein said nozzle body is repositionable about said central axis of said tubular member.

\* \* \* \* \*